(12) United States Patent
Ukawa et al.

(10) Patent No.: US 7,604,838 B2
(45) Date of Patent: Oct. 20, 2009

(54) METHOD OF MAKING STABLY PRESERVED MICROSPHERES IN LOWER ALCOHOL SOLVENT

(75) Inventors: Hisashi Ukawa, Tokyo (JP); Akio Yamane, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 12/216,451

(22) Filed: Jul. 3, 2008

(65) Prior Publication Data

US 2008/0272507 A1 Nov. 6, 2008

Related U.S. Application Data

(62) Division of application No. 11/438,625, filed on May 23, 2006, now abandoned.

(30) Foreign Application Priority Data

Jun. 23, 2005 (JP) .............................. 2005-182897

(51) Int. Cl.
*B01J 8/00* (2006.01)
*B32B 5/16* (2006.01)
(52) U.S. Cl. .................. 427/222; 427/301; 427/322; 427/337; 424/490
(58) Field of Classification Search ............... 427/222, 427/301, 322, 337; 424/490
See application file for complete search history.

(56) References Cited

U.S. PATENT DOCUMENTS

| 4,259,313 A | 3/1981 | Frank et al. |
| 4,267,235 A | 5/1981 | Rembaum et al. |
| 4,283,382 A | 8/1981 | Frank et al. |
| 4,539,385 A | 9/1985 | Geist et al. |
| 5,073,498 A | 12/1991 | Schwartz et al. |
| 5,395,688 A | 3/1995 | Wang et al. |
| 6,193,953 B1 * | 2/2001 | Lohrmann et al. ......... 424/9.52 |
| 6,306,975 B1 | 10/2001 | Zhao et al. |
| 6,602,692 B1 | 8/2003 | Glusenkamp et al. |
| 6,964,747 B2 | 11/2005 | Banerjee et al. |

FOREIGN PATENT DOCUMENTS

| EP | 0 154 734 | 3/1984 |
| EP | 1 435 520 A1 | 9/2002 |

OTHER PUBLICATIONS

European Search Report dated Sep. 20, 2006.
Lei, Han et al. "The preparation and catalytically active characterization of papain immobilized on magnetic composite microspheres" Elsevier, Enzyme and Microbial Technology, Mar. 3, 2004, pp. 15-21.

* cited by examiner

*Primary Examiner*—H. (Holly) T Le
(74) *Attorney, Agent, or Firm*—Stites & Harbison PLLC; Juan Carlos A. Marquez, Esq.

(57) ABSTRACT

Active carboxylic acid ester groups are coupled on the surfaces of microspheres so as to reduce protocols for microsphere processing, control side reactions, and stably preserve beads containing active carboxylic acid ester groups. Further, microspheres labeled with at least one fluorescent dye cage in the microspheres, and the microspheres are preserved in lower alcohol.

9 Claims, 9 Drawing Sheets

Prior Art  FIG. 3

```
┌─────────────────────────────────────────────────────────────────────────────────┐
│ Vortex bead stocks, and then conduct sonication for about 20 seconds so as to   │
│ suspend them.                                                                    │
└─────────────────────────────────────────────────────────────────────────────────┘
                                      ⇩
┌─────────────────────────────────────────────────────────────────────────────────┐
│ Weigh about 400 μl of the suspension of beads (equivalent to $5 \times 10^8$ beads). │
└─────────────────────────────────────────────────────────────────────────────────┘
                                      ⇩
┌─────────────────────────────────────────────────────────────────────────────────┐
│ Centrifuge the suspension at 8000 xg for about 5 minutes so as to remove        │
│ supernatant thereof.                                                             │
└─────────────────────────────────────────────────────────────────────────────────┘
                                      ⇩
┌─────────────────────────────────────────────────────────────────────────────────┐
│ Suspend the resultant in 100 μl of sterilized water, vortex it, and then        │
│ conduct sonication for about 20 seconds.                                        │
└─────────────────────────────────────────────────────────────────────────────────┘
                                      ⇩
┌─────────────────────────────────────────────────────────────────────────────────┐
│ Centrifuge the suspension at 8000 xg for about 2 minutes so as to remove        │
│ supernatant thereof.                                                             │
└─────────────────────────────────────────────────────────────────────────────────┘
                                      ⇩
┌─────────────────────────────────────────────────────────────────────────────────┐
│ Suspend the resultant in 50 μl of a 0.1M MES solution (pH 4.5), vortex it, and  │
│ then conduct sonication for about 20 seconds.                                   │
└─────────────────────────────────────────────────────────────────────────────────┘
                                      ⇩
┌─────────────────────────────────────────────────────────────────────────────────┐
│ Add 2 μl of 100 μM oligonucleotide to the suspension of beads and vortex it.    │
└─────────────────────────────────────────────────────────────────────────────────┘
                                      ⇩
┌─────────────────────────────────────────────────────────────────────────────────┐
│ Add 2.5 μl of an EDC solution (10 mg/ml) to the suspension and vortex it.       │
└─────────────────────────────────────────────────────────────────────────────────┘
                                      ⇩
┌─────────────────────────────────────────────────────────────────────────────────┐
│ Incubate the suspension of beads in a dark place at room temperature for        │
│ about 30 minutes.                                                                │
└─────────────────────────────────────────────────────────────────────────────────┘
                                      ⇩
┌─────────────────────────────────────────────────────────────────────────────────┐
│ Add 2.5 μl of an EDC solution (10 mg/ml) to the suspension and vortex it.       │
└─────────────────────────────────────────────────────────────────────────────────┘
                                      ⇩
┌─────────────────────────────────────────────────────────────────────────────────┐
│ Incubate the suspension of beads in a dark place at room temperature for        │
│ about 30 minutes.                                                                │
└─────────────────────────────────────────────────────────────────────────────────┘
                                      ⇩
┌─────────────────────────────────────────────────────────────────────────────────┐
│ Add 1 ml Tween20 (0.02% v/v) to the suspension and vortex it.                   │
└─────────────────────────────────────────────────────────────────────────────────┘
                                      ⇩
┌─────────────────────────────────────────────────────────────────────────────────┐
│ Centrifuge the suspension at 8000 xg for about 2 minutes so as to remove        │
│ supernatant thereof.                                                             │
└─────────────────────────────────────────────────────────────────────────────────┘
                                      ⇩
┌─────────────────────────────────────────────────────────────────────────────────┐
│ Add 1 ml SDS (0.1% w/v) to the resultant and vortex it.                         │
└─────────────────────────────────────────────────────────────────────────────────┘
                                      ⇩
┌─────────────────────────────────────────────────────────────────────────────────┐
│ Centrifuge the resultant at 8000 xg for about 2 minutes so as to remove         │
│ supernatant thereof.                                                             │
└─────────────────────────────────────────────────────────────────────────────────┘
                                      ⇩
┌─────────────────────────────────────────────────────────────────────────────────┐
│ Suspend the resultant in a 100 ml of TE (pH 8.0), vortex it, and then conduct   │
│ sonication for about 20 seconds.                                                │
└─────────────────────────────────────────────────────────────────────────────────┘
```

FIG. 7  *Prior Art*
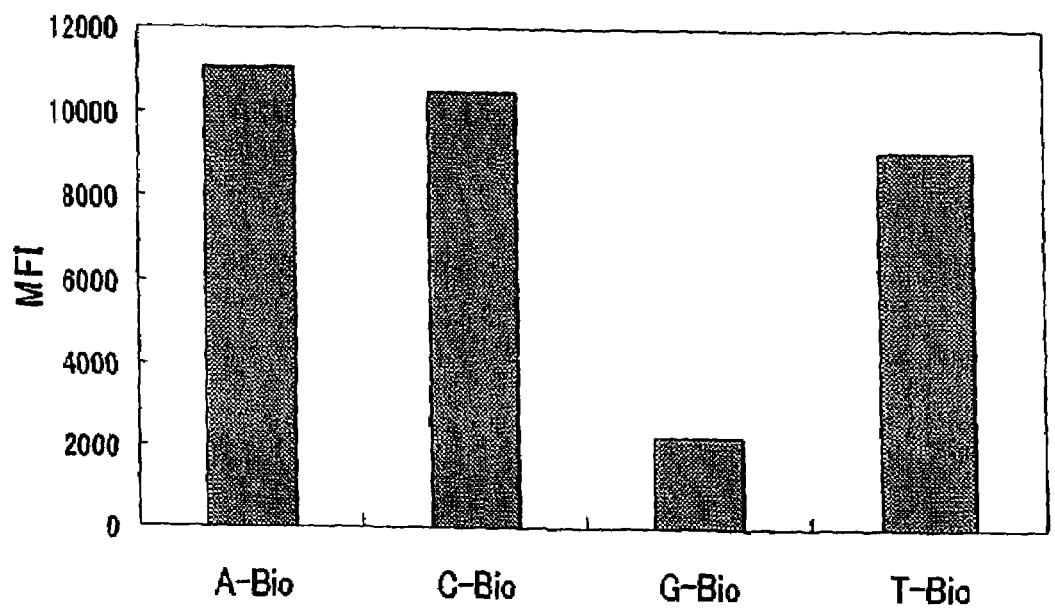
FIG. 8
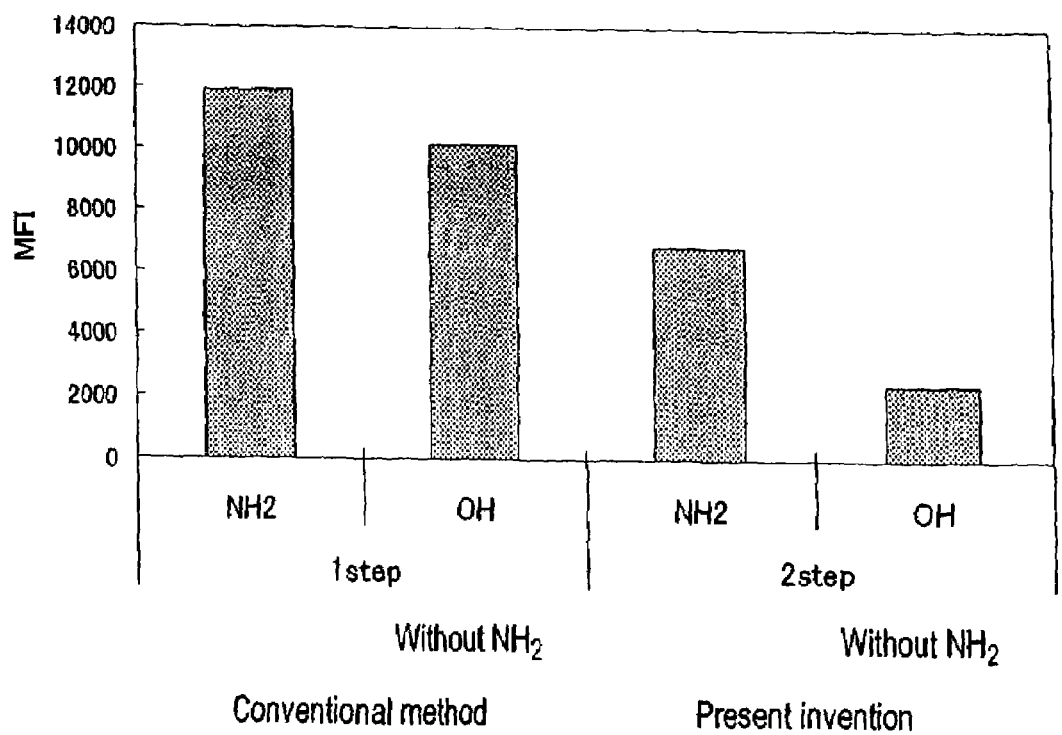

METHOD OF MAKING STABLY PRESERVED MICROSPHERES IN LOWER ALCOHOL SOLVENT

CROSS REFERENCE TO RELATED APPLICATIONS

This application is a Divisional application of U.S. application Ser. No. 11/438,625 filed May 23, 2006 now abandoned. Priority is claimed based on U.S. application Ser. No. 11/438,625 filed May 23, 2006, which claims the priority date of Japanese Patent Application No. 2005-182897 filed Jun. 23, 2005, all of which is incorporated by reference.

BACKGROUND OF THE INVENTION

1. Field of the Invention

In general, the present invention is applied to flow cytometry technique. The present invention relates to microspheres, which usually has a diameter of 100 μm or less and is filled with multicolor fluorecent. More specifically, the present invention relates to microspheres that activated esters are held and stabilized on the surface without fluorescence seeping and polymer molecules filled with at least one type of fluorescent dye.

2. Background Art

Polymer particles, filled with fluorescent dye, are often used as a marker or indicator in various biomedical assays. "Microspheres" are minute particles basically having total diameters within micrometer-size. Microspheres can be analyzed with manual techniques or other methods known in the art. Preferably, automation technologies such as flow cytometry disclosed in U.S. Pat. No. 4,665,024 described below, the patent for which was granted to Mansour et al., can be used for analysis of such particles.

Hitherto, biomolecules such as proteins (e.g. antigens and antibodies), nucleic acids, peptides, and sugar chains have been coupled to microparticles filled with at least one color of fluorescent dye. They have been used quantitative analysis of biomolecules or genetic polymorphism analysis. A plurality of analytical items can be simultaneously analyzed by a number of microspheres filled with fluorescent dye of different density and coupled with different types of biomolecules.

The surfaces of microspheres are covered with carboxyl groups. A carboxyl group can form an amide bond with an amino group in a biomolecule via dehydration-condensation reaction. This reaction is used to couple biomolecules on microspheres. However, since the reactivity of carboxyl groups is low, it is necessary to activate the carboxyl groups in some way. There are various types of reagents capable of activating carboxyl groups. Meanwhile, the aforementioned microspheres are filled with at least one fluorescent dye in which fluorescent dye is prone to seep into organic solvent. Thus, the reaction should be carried out in an aqueous solution. EDC (1-ethyl-3-(3-dimethylaminopropyl)carbodiimide hydrochloride) is the only reagent capable of activating carboxyl groups in an aqueous solution. In addition, it is necessary for biomolecules to contain primary amino groups so that they react with activated carboxylic acid esters. In particular, biomolecues such as nucleic acids, sugar chains that have no primary amino groups are necessary to introduce primary amino group into those biomolecule prior to the conjugation.

EDC is a reagent capable of activating carboxyl groups in an acid solvent. The coupling reaction solvent is limited to one used in acidic conditions. However, some types of biomolecules can stably exist only in basic conditions. Thus, the types of biomolecules cannot couple on microspheres. In addition, when nucleic acid couples with microspheres using EDC, EDC may react with amino group of nucleobases under acidic condition.

The following examples pertain to conventional methods for immobilizing biomolecules on fluorescent stained microparticles: a) method for coupling with a biomolecule after activating carboxyl groups carried on the surface of a microsphere to result in succinimide esters; and b) method for coupling with a biomolecule when simultaneously activating carboxyl groups carried on the surface of a microparticle to result in carbodiimide esters.

In the method for activating carboxyl groups to result in succinimide esters described in above a), NHS (N-hydroxysuccinimide) and EDC are added to a suspension of microparticles so as to activate carboxyl groups to result in hydroxysuccinimide esters. The method involves the instantaneous immobilization of a biomolecule on a microparticle, the surface of which has been activated.

In the method for activating carboxyl groups to result in carbodiimide esters described in above b), EDC and biomolecules are simultaneously added to a suspension of microparticles. The method involves the activation of carboxyl groups on the surfaces of microspheres to result in carbodiimide esters such that biomolecules instantaneously react with the active esters, leading to immobilization of the biomolecules on the microspheres.

Active carboxylic acid ester groups such as hydroxysuccinimide ester groups react with hydroxyl groups in an aqueous solution so as to again become carboxyl groups. This reaction is extensively observed, particularly under basic conditions. However, hydroxysuccinimide ester groups are relatively stable in organic solvent without water.

Microspheres are filled with fluorescent dyes in which fluorescent dyes are prone to seep into hydrophobic organic solvents such as aromatic hydrocarbon, pyridine, and dioxane.

JP Patent Publication (Kohyo) Nos. 2001-520323 A and 2002-501184 A described below are known technical literature with regard to methods for producing or using fluorescent stained microparticles.

SUMMARY OF THE INVENTION

When coupling with biomolecules such as proteins (e.g. antigens and antibodies), nucleic acids, sugar chains, and peptides on the surfaces of microparticles (microspheres), EDC and NHS, both of which are unstable in the atmosphere and are handled with difficulty, must be used.

It is necessary to carry out the reaction whereby biomolecules are coupled on the surfaces of microspheres using EDC under acidic conditions. Thus, for example, peptides that are soluble only in a basic solvent cannot be coupled, resulting in a limitation in terms of the selection of biomolecules that can be coupled.

In a reaction whereby nucleic acids are coupled on the surfaces of microspheres using EDC, side reactions those may be the reaction of amino group of nucleobases and EDC activated carboxyl group cannot be suppressed, because of stringent reaction conditions. In such case, as a result of a side reaction, nucleic acids that are used for probe are coupled at nonspecific sites or multiple sites so as to largely influence the probe function especially in the single nucleotide polymorphism identification.

In a reaction whereby biomolecules are coupled on the surfaces of microspheres using EDC and NHS (or sulfo-NHS (N-Hydroxysulfosuccinimide)), since activated carboxylic acid ester groups are unstable, the coupling reaction must be carried out immediately after activation of carboxyl groups. In addition, when 2,3,5,6-tetrafluorophenol and 4-sulfo-2,3,5,6-tetrafluorophenol are used instead of NHS-, resulted carboxyl esters are relatively stable. However, the conjugation reaction between those esters and biomolecule which contain primary amino group is very slow.

Activated carboxylic acid ester groups can be stable in an organic solvent; however, fluorescent dyes on microspheres become eluted, which ruin the function of microsphere. This is due to the hydrophobicity of fluorescent dyes on microspheres.

It is an objective of the present invention to provide a technique whereby activated carboxylic acid ester groups are stabilized on the surfaces of microspheres without fluorescent dye seeping so as to simplify protocols for the conjugation between biomolecules and microspheres, extend the type of applicable peptide.

Inventors of the present invention have found that the above problems can be solved by activating carboxyl groups on the surfaces of microspheres in advance to result in active esters and preserving them in lower alcohol. This has led to the completion of the present invention.

The present invention relates to stabilization of activated carboxyl group on microspheres which is labeled with at least one fluorescent dye caged into the microspheres, and the microspheres are preserved in lower alcohol.

In particular, the microspheres are covered with a functional group such as a carboxyl group.

Further, the carboxyl group is activated to result in hydroxysuccinimide ester.

The lower alcohol includes 1-butanol, methanol, ethanol, n-propanol, and isopropanol. In the present invention, isopropanol and 1-butanol are more preferable.

Preferably, in the present invention, the functional group that activates a carboxyl group includes a succinimidyl ester group, a sulfo-succinimidyl ester group, a 2,3,5,6-tetrafluorophenol ester group, and a 4-sulfo-2,3,5,6-tetrafluorophenol ester group.

Microspheres, labeled with at least one type of fluorescent dye, is preserved in lower alcohol such that the activated carboxyl group bonded to microspheres can be stabilized over a long period of time. The microspheres are covered with carboxyl groups that are activated by a succinimidyl ester group, a sulfo-succinimidyl ester group, a 2,3,5,6-tetrafluorophenol ester group, a 4-sulfo-2,3,5,6-tetrafluorophenol ester group, and the like.

In the reaction of the activated carboxyl group a reaction buffer conducting a coupling reaction are substituted for lower alcohol. Then, the microparticles are coupled with biomolecules on the surfaces of the microspheres. Thus, biomolecules such as antibodies, antigens, nucleic acids, sugar chains, and peptides can be coupled under the respective optimum conditions. In addition, side reactions caused by nucleic acids can be significantly suppressed.

BRIEF DESCRIPTION OF THE DRAWINGS

FIG. 3 shows a flowchart of conventional protocols for nucleic acids coupling following activation of the surfaces of microspheres.

FIG. 7 shows results obtained by coupling biotinylated homooligonucleotide 20-mers of A, C, G, and T on microparticles using protocols of a conventional method.

FIG. 8 shows a graph indicating the results of Example 1.

DESCRIPTION OF THE PREFERRED EMBODIMENTS

Figure 1:
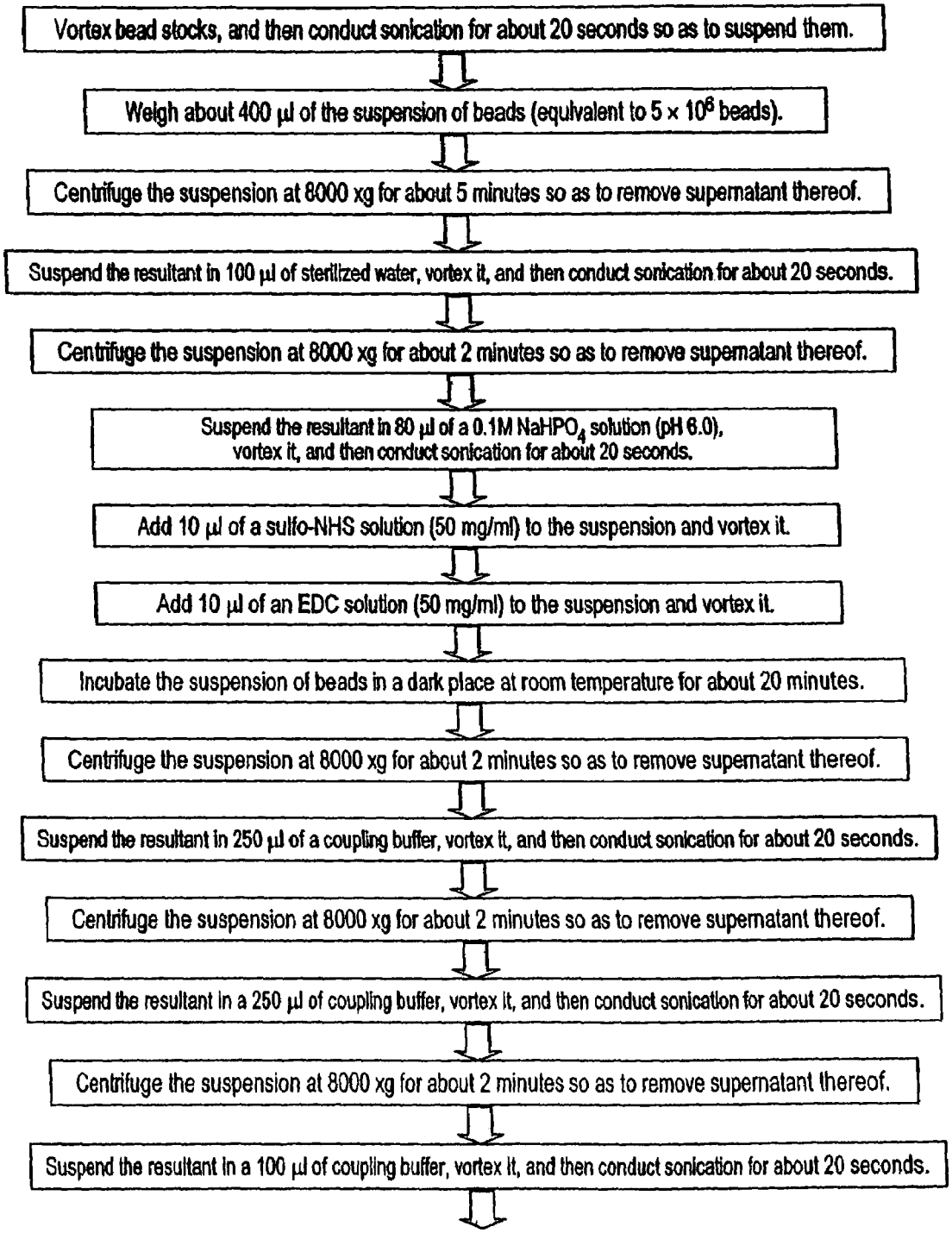
FIG. 1 shows a flowchart of conventional protocols for activation of the surfaces of microspheres upon protein coupling.

FIG. 1 shows conventional protocols for activation of the surfaces of microparticles for protein coupling. To couple proteins on microspheres, carboxyl groups on the surfaces of microparticles are activated to result in active carboxylic acid ester groups using EDC and NHS (or sulfo-NHS). Here, a 0.1M sodium phosphate solution (pH 6.0), a 0.05 M MES (2-(N-morpholino) ethane sulfonic acid) solution (pH 6.0), or the like is used as a buffer for a reaction to form active carboxylic acid ester groups. After the reaction for forming active esters finished, instantaneously, a protein coupling reaction shown in FIG. 2 must be carried out.

Figure 2:
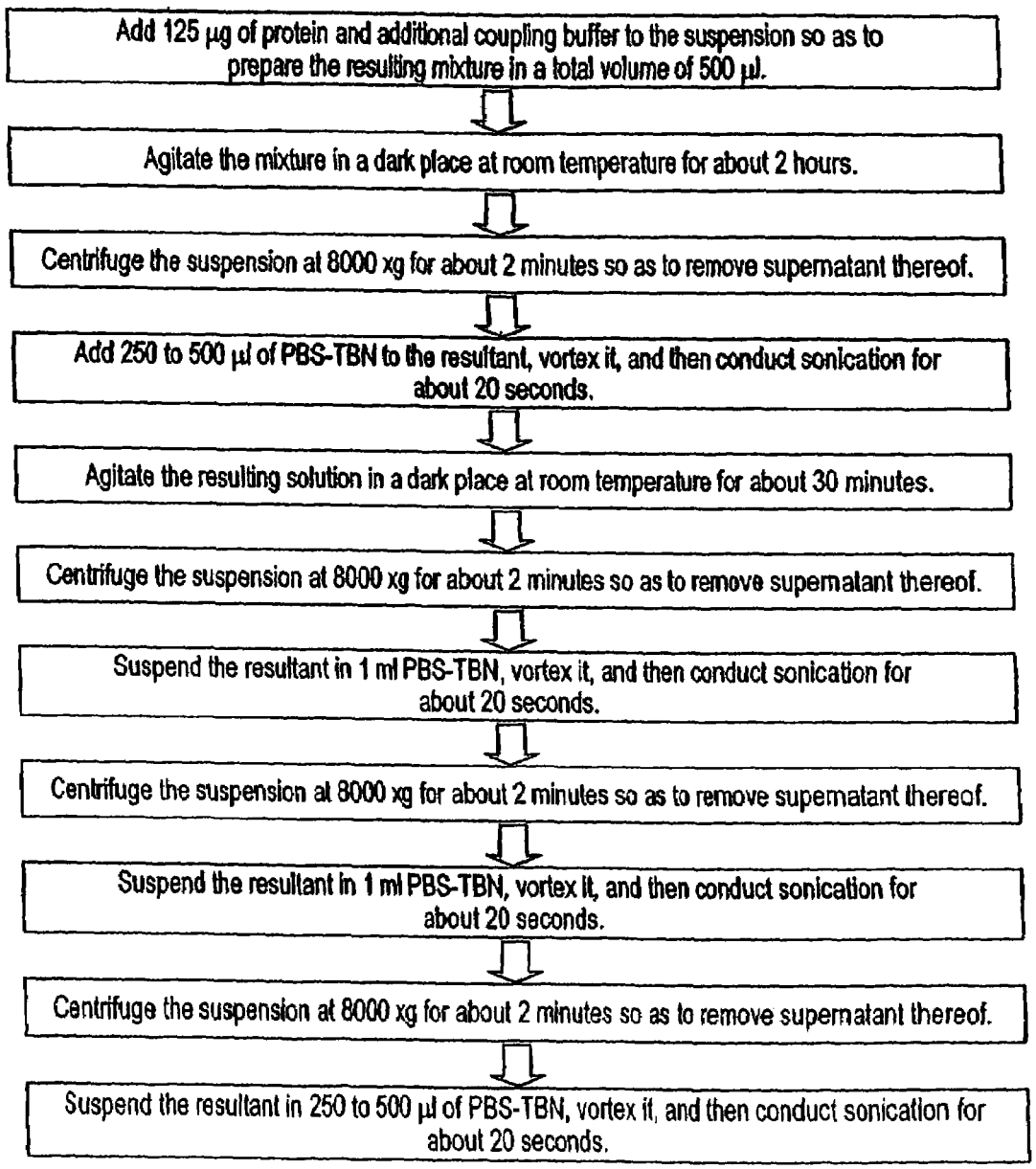
FIG. 2 shows a flowchart of conventional protocols for protein coupling following activation of the surfaces of microspheres.

FIG. 2 shows conventional general protocols for a reaction to couple proteins and active carboxylic acid ester on the surfaces of microspheres. Amino groups of proteins react with active carboxylic acid ester groups, resulting in formation of amide bonds. Thus, proteins were coupled on the surfaces of microspheres. A PBS (phosphate buffered saline: pH 7.4) and 0.05 M MES (pH 6.0) solution or the like is used as a buffer for carrying out a protein coupling reaction. After the coupling reaction finished, blocking and washing are carried out using a PBS-TBN (PBS; 1% BSA (bovine serum albumin); 0.02% Tween (registered trademark: ICI Americas) 20; and 0.05% sodium azide) solution. At the end, processed microspheres are preserved in a PBS-TBN solution.

FIG. 3 shows conventional protocols for microparticle processing for nucleic acid immobilization. In the case of nucleic acid, it is necessary to modify nucleic acid with a primary amino group via a linker. By allowing EDC to react with carboxylic acid on microspheres, carboxyl groups on microspheres become carbodiimide esters, such that nucleic acid can be coupled on the surfaces of microspheres by reaction of the carbodiimide with the primary amino group introduced to nucleic acids. For this reaction, a 0.1 M MES solution (pH 4.5) is used as a reaction solution. After termination of the coupling reaction, activated surface of microspheres is blocked using a 0.02% Tween 20 solution (registered trademark), and washing is carried out using a 0.1% SDS (sodium dodecyl sulfate) solution. Processed microspheres are preserved in a TE (Tris-EDTA) solution (pH 8.0). Note that a side reaction, whereby coupling occurs at various amino group of nucleobase, cannot be controlled.

Figure 4:
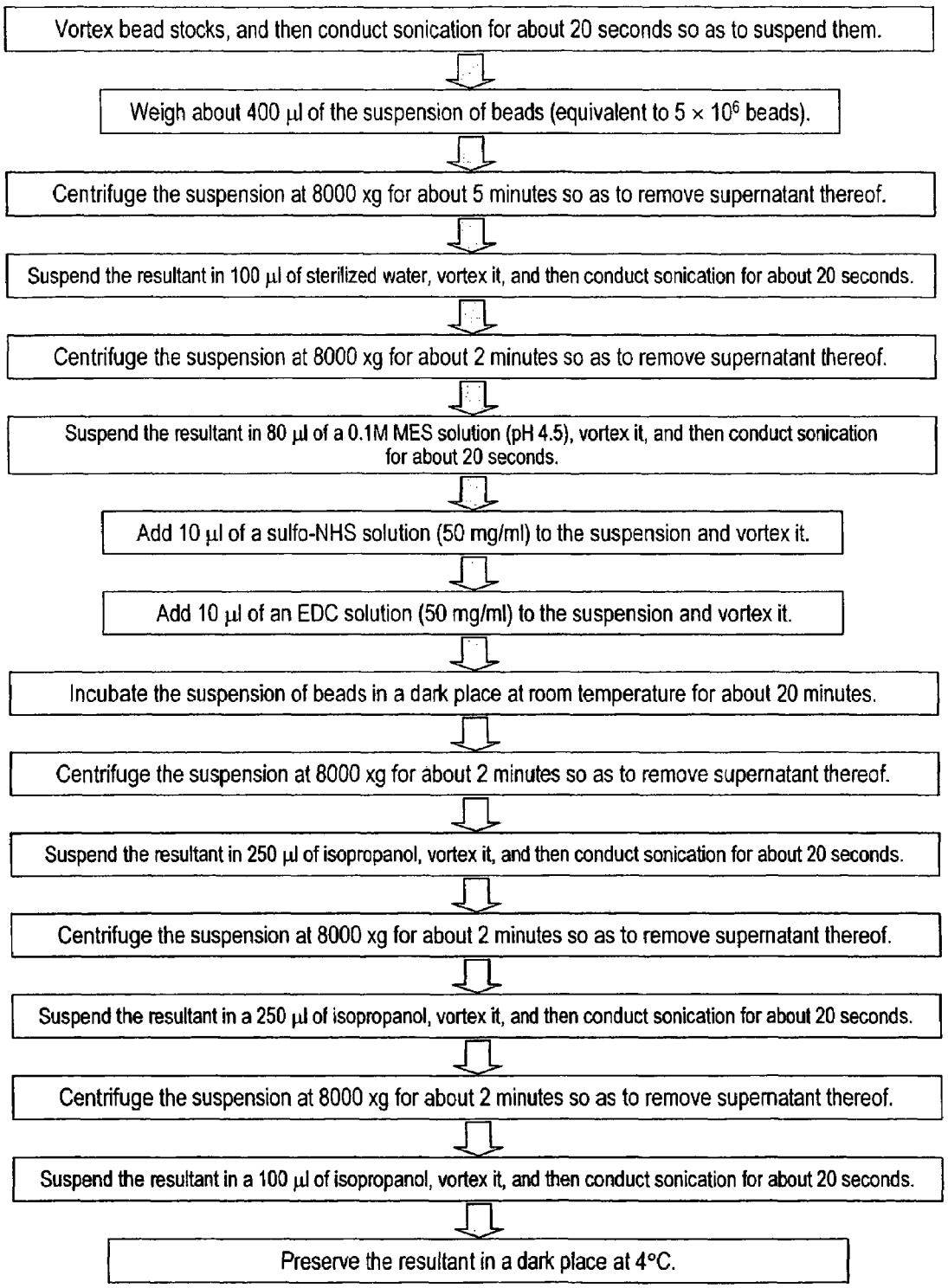
FIG. 4 shows a flowchart of a method for producing microspheres covered with active carboxylic acid esters.

FIG. 4 shows a method for producing microspheres on the surfaces of which active carboxylic acid ester groups are coupled. The reaction for forming active carboxylic acid ester groups is almost the same as that of a conventional method. However, this method significantly differs from that of a conventional method in that the resulted microspheres having active carboxylic acid ester groups are preserved in isopropanol, so as to maintain carboxylic acid ester groups stably.

Figure 5:
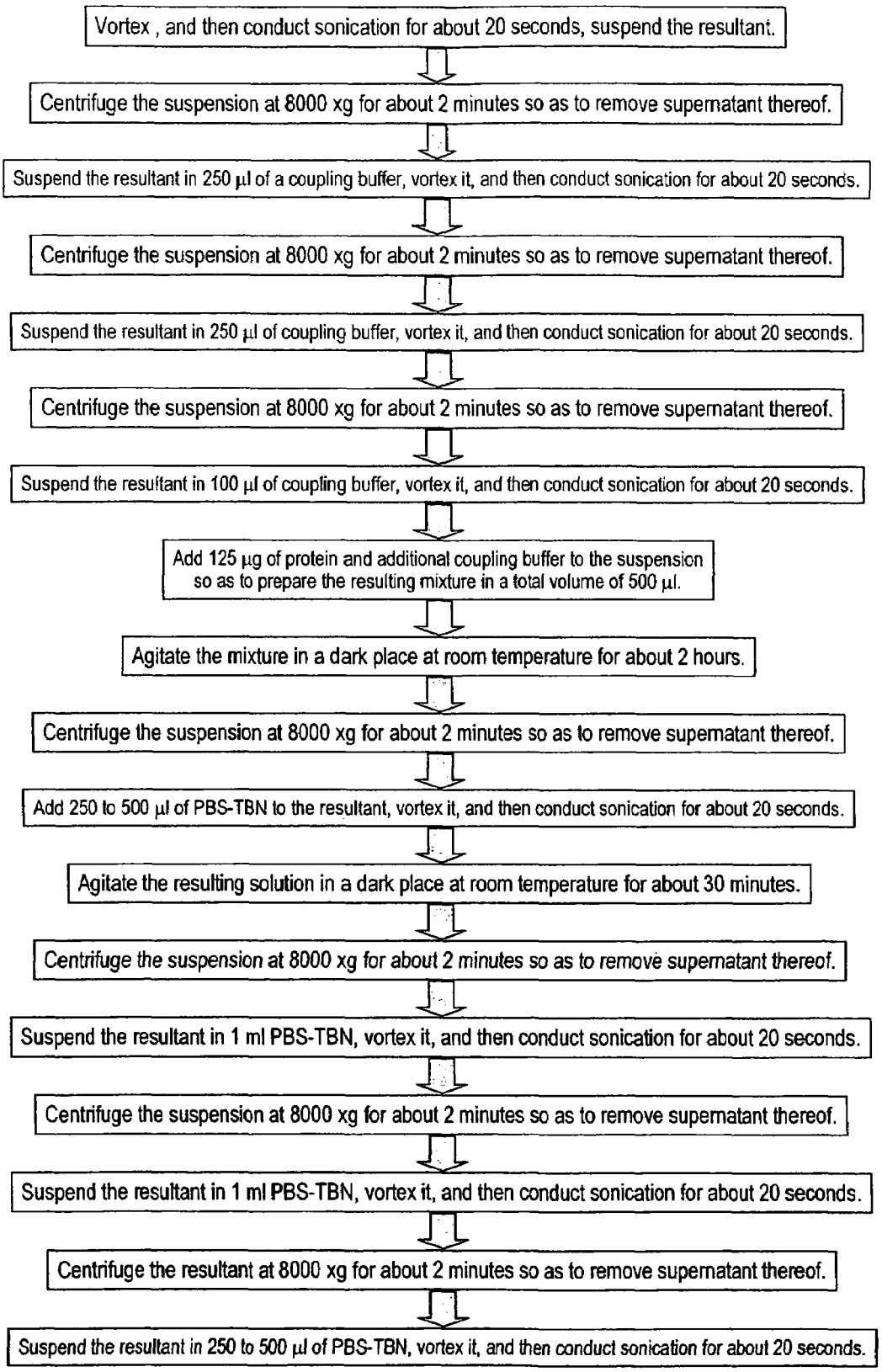
FIG. 5 shows a flowchart of protocols for microsphere processing for protein coupling in accordance with the present invention.

FIG. 5 shows protocols for protein processing using microspheres produced in accordance with the present invention. In these protocols, PBS (pH 7.4) or the like is used as a coupling buffer. Thus, by carrying out solvent substitution, proteins can instantaneously be coupled on the surfaces of microspheres. Therefore, the protocols can be significantly reduced compared with those shown in FIGS. 1 and 2.

Figure 6:
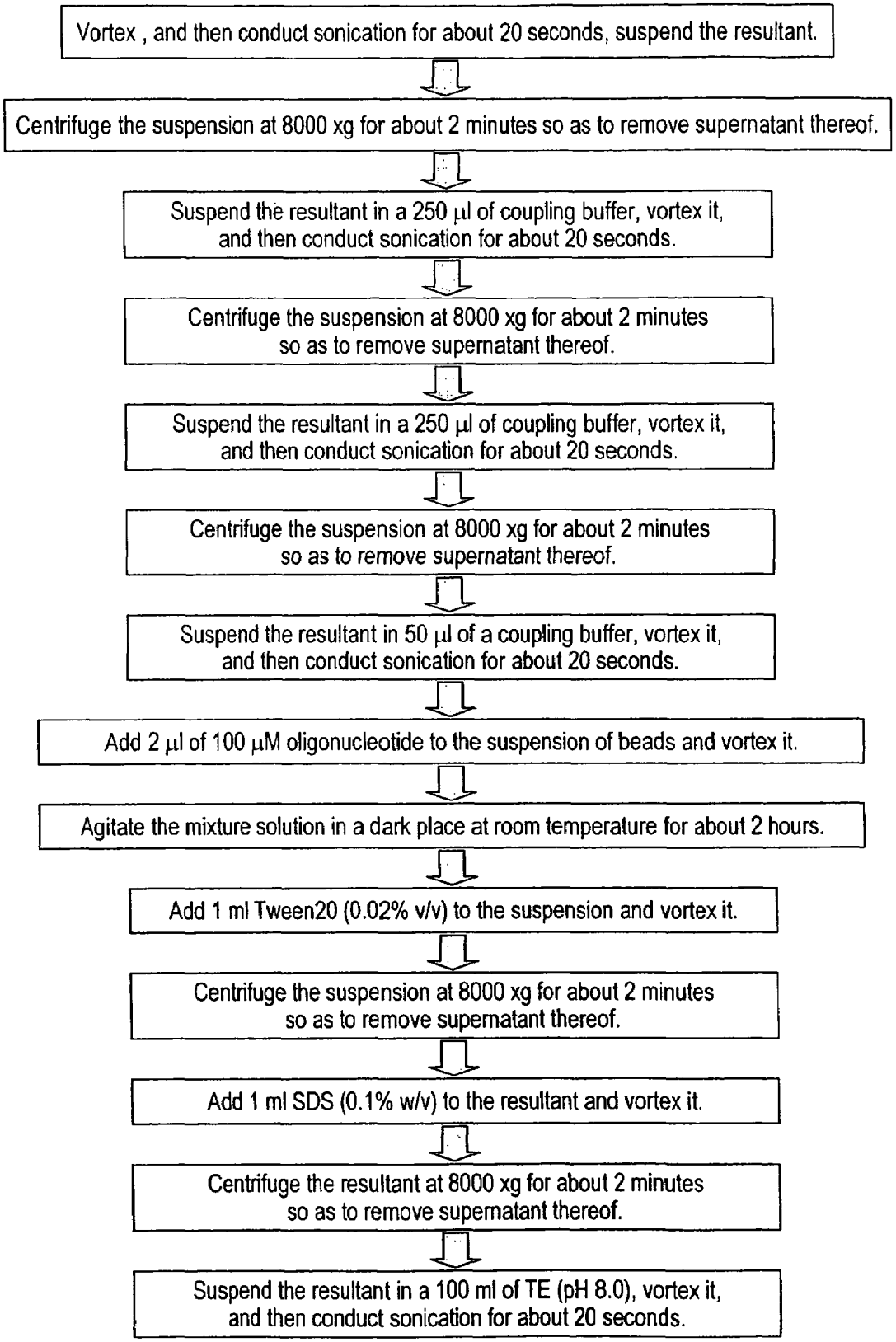
FIG. 6 shows a flowchart of protocols for microsphere processing for nucleic acid coupling in accordance with the present invention.

FIG. 6 shows protocols for nucleic acid processing using microspheres produced in accordance with the present invention. In the protocols, 0.1 M phosphate buffer (pH 8.0) or the like is used as coupling buffer upon coupling of nucleic acid. Since the reaction is carried out under mild conditions, the side reaction that takes place in FIG. 3 can be suppressed.

EXAMPLES

Comparative Example 1

Using conventional protocols, biotinylated homooligonucleotide 20-mers of A, C, G, and T, the ends of which had not been modified with primary amino group, were coupled on microparticles. The processed microparticles are conducted to detect the biotinylated homooligonucleotide using Luminex 100™. The result showed that fluorescent signal intensity of biotinylated homooligonucleotide 20-mers of A, C, and T coupled on the microparticles without modification of primary amino group that were the same as in the case of oligonucleotide with modification of primary amino group (FIG. 7).

Example 1

A coupling reaction was performed on biotinylated oligonucleotide 20-mers, in which primary amino group had not been introduced, using microspheres activated in accordance with the present invention, as shown in FIG. 6. The results were compared with those obtained by a conventional method. Then, the side reaction was found to have been significantly suppressed compared with that in the conventional method (FIG. 8).

Example 2

Figure 9:
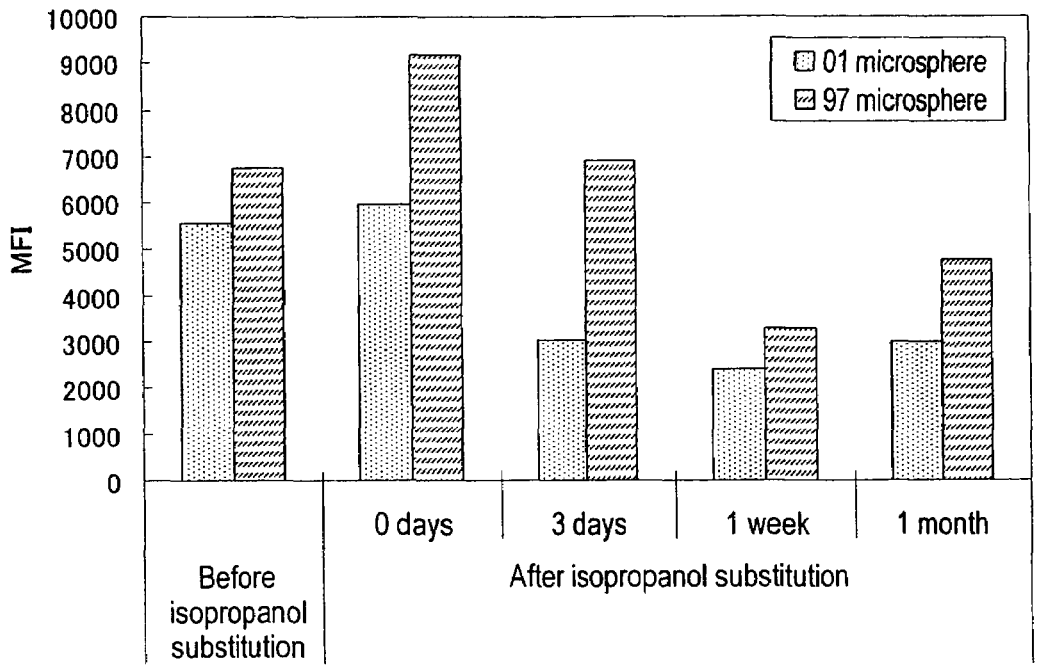
FIG. 9 shows a graph indicating the results of Example 2.

Nucleic acids were immobilized using microspheres produced in accordance with the present invention, as shown in FIG. 6. Conjugation of primary amino group introduced in nucleic acids with activated microspheres were performed in the various condition such as before, immediately after, and 3 days, 1 week, and 1 month after substitution using an isopropanol solvent. The experiment was carried out to confirm the presence or absence of fading of fluorescent intensity of dyes in isopropanol and the presence or absence of activity retention of active carboxylic acid ester groups (FIG. 9). The identification of a bead (e.g., #01) and a bead (e.g., #97) were performed ordinarily as in those without isopropanol treatment. Therefore, fluorescent dyes do not seep out during the preservation in isopropanol. Even after one month, about half of the activated ester had been maintained.

Example 3

Figure 10:
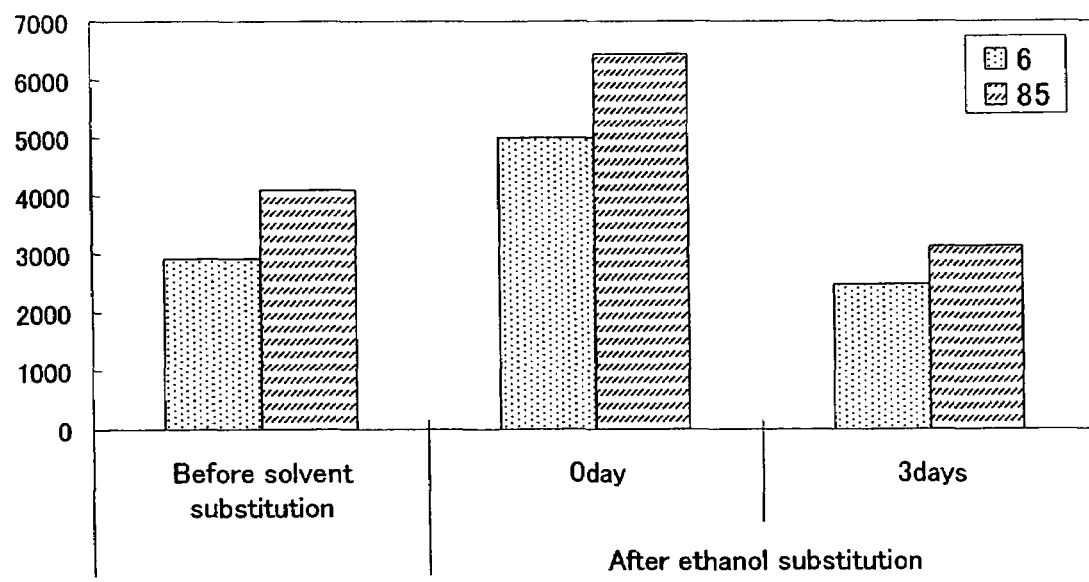
FIG. 10 shows a graph indicating the results of Example 3.

Nucleic acids were immobilized as shown in FIG. 6, using microspheres produced in accordance with the present invention. Conjugation of primary amino group introduced in nucleic acids with activated microspheres was performed in the various condition such as before, immediately after, and 3 days after substitution using an ethanol solvent. The experiment was carried out to confirm the presence or absence of fading of fluorescent intensity of dyes in ethanol and the presence or absence of activity retention of active carboxylic acid ester groups (FIG. 10). The identification of a bead (e.g., #6) and a bead (e.g., #85) were performed ordinarily as in those without ethanol treatment. However, about half of the activated ester had been degraded even in 3 days.

Example 4

Figure 11:
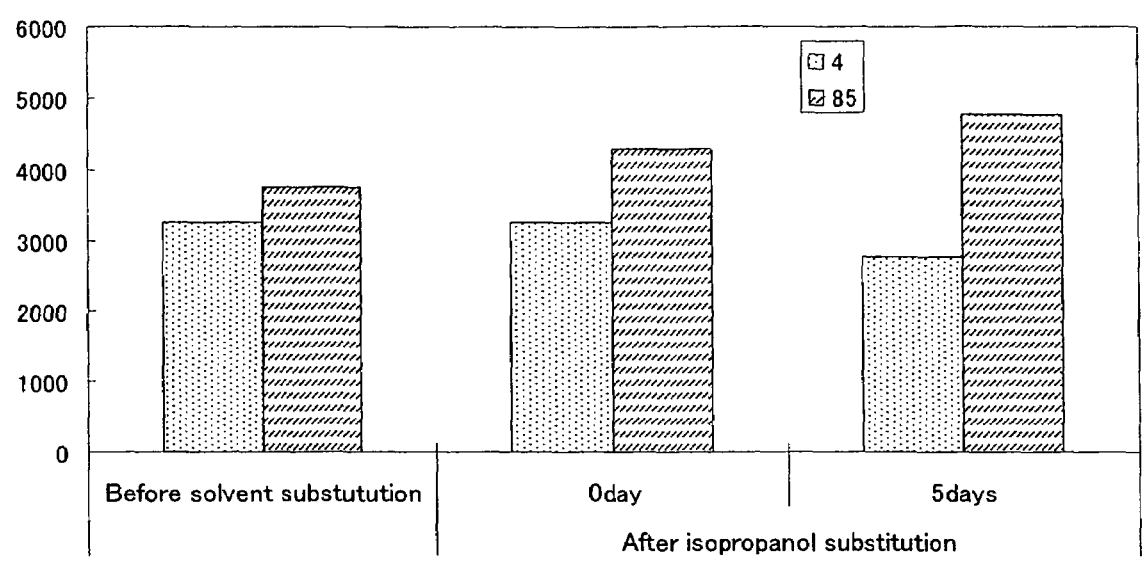
FIG. 11 shows a graph indicating the results of Example 4.

Nucleic acids were immobilized as shown in FIG. 6, using microspheres produced in accordance with the present invention. Conjugation of primary amino group introduced in nucleic acids with activated microspheres was performed in the various condition such as before, immediately after, and 5 days after substitution using a 1-butanol solvent. The experiment was carried out to confirm the presence or absence of fading of fluorescent intensity of dyes in 1-butanol and the presence or absence of activity retention of active carboxylic acid ester groups (FIG. 11). The identification of a bead (e.g., #4) and a bead (e.g., #85) were performed ordinarily as in those without butanol treatment. After 5 days from preparation, the activity of the ester had not been changed virtually.

In the present invention, active carboxylic acid ester groups are immobilized on the surfaces of microspheres. Thus, in accordance with the present invention, protocols for microsphere processing can be improved such that side reactions can be controlled and microspheres (beads) having active carboxylic acid ester groups can be stably preserved. As a result, the use of microspheres is promoted in the field of biochemistry.

What is claimed is:

1. A method of stabilizing activated carboxyl groups on microspheres, comprising the steps of:
    activating carboxyl groups thereby forming active esters;
    covering microspheres with the active esters;
    filling the covered microspheres with at least one fluorescent dye; and
    storing the microspheres in a solvent which consists of lower alcohol,
    wherein the lower alcohol is selected from the group consisting of 1-butanol, methanol, ethanol, n-propanol, and isopropanol.

2. The method according to claim 1, wherein the carboxyl group is activated to result in hydroxysuccinimide ester.

3. The method according to claim 1, wherein the lower alcohol is isopropanol or 1-butanol.

4. The method according to claim 1, wherein the carboxyl group is activated with at least one of a succinimidyl ester group and a sulfa-succinimidyl ester group.

5. The method according to 1, wherein the carboxyl group is activated with at least one of a 2,3,5,8-tetrafluorophenol ester group and a 4-sulfo-2,3,5,6-tetrafluorophenol ester group.

6. The method according to 1, further comprising: repeatedly suspending the solvent with phosphate buffered saline (PBS) as a coupling buffer thereby coupling proteins onto surfaces of the microspheres stored in the solvent.

7. The method according to 6, wherein the PBS is at pH 7.4.

8. The method according to 1, further comprising: repeatedly using a phosphate buffer solution as a coupling buffer thereby coupling nucleic acids onto surfaces of the microspheres stored in the solvent.

9. The method according to 8, wherein the phosphate buffer solution is 0.1 M phosphate buffer at pH 8.0.

* * * * *